United States Patent
Romoda et al.

(10) Patent No.: US 8,721,702 B2
(45) Date of Patent: May 13, 2014

(54) INTRAOCULAR SHUNT DEPLOYMENT DEVICES

(75) Inventors: Laszlo O. Romoda, San Clemente, CA (US); Christopher Horvath, Desert Hot Springs, CA (US)

(73) Assignee: AqueSys, Inc., Aliso Viejo, CA (US)

( * ) Notice: Subject to any disclaimer, the term of this patent is extended or adjusted under 35 U.S.C. 154(b) by 541 days.

(21) Appl. No.: 12/946,645

(22) Filed: Nov. 15, 2010

(65) Prior Publication Data

US 2012/0123439 A1  May 17, 2012

(51) Int. Cl.
*A61F 2/06* (2013.01)

(52) U.S. Cl.
USPC .............. 623/1.11; 606/107; 606/108; 604/8; 604/9

(58) Field of Classification Search
USPC .......... 623/1.11, 1.41, 8, 9, 10; 606/107, 108, 606/166–170; 604/8, 9
See application file for complete search history.

(56) References Cited

U.S. PATENT DOCUMENTS

| | | |
|---|---|---|
| 3,788,327 A | 1/1974 | Donowitz et al. |
| 3,960,150 A | 6/1976 | Hussain et al. |
| 4,722,724 A | 2/1988 | Schocket |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,863,457 A | 9/1989 | Lee |
| 4,902,292 A | 2/1990 | Joseph |
| 4,911,161 A | 3/1990 | Schechter |
| 4,915,684 A | 4/1990 | Mackeen et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Federov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,178,604 A | 1/1993 | Baerveldt et al. |
| 5,180,362 A * | 1/1993 | Worst ................................ 604/8 |

(Continued)

FOREIGN PATENT DOCUMENTS

| | | |
|---|---|---|
| WO | WO 98/23237 | 6/1998 |
| WO | WO 02/74052 | 9/2002 |
| WO | WO-2007/087061 A2 | 8/2007 |

OTHER PUBLICATIONS

International Search Report in PCT application No. PCT/US2007/072547, mailed May 23, 2008, 7 pages.
Written Opinion in PCT application No. PCT/US2007/072547, mailed Dec. 31, 2008, 8 pages.
International Preliminary Report on Patentability in PCT application No. PCT/US2007/072547, mailed Jun. 1, 2009, 9 pages.

(Continued)

*Primary Examiner* — Darwin Erezo
*Assistant Examiner* — Katrina Stransky
(74) *Attorney, Agent, or Firm* — James W. Hill; Nathan S. Smith; McDermott Will & Emery LLP

(57) ABSTRACT

The invention generally relates to devices for deploying an intraocular shunt within an eye. In certain embodiments, devices of the invention include a housing, a deployment mechanism at least partially disposed within the housing, and a hollow shaft coupled to the deployment mechanism, in which the shaft is configured to hold an intraocular shunt, and in which rotation of the deployment mechanism results in deployment of the shunt.

44 Claims, 13 Drawing Sheets

(56) References Cited

U.S. PATENT DOCUMENTS

| | | |
|---|---|---|
| 5,275,622 A | 1/1994 | Lazarus et al. |
| 5,290,295 A | 3/1994 | Querals et al. |
| 5,300,020 A | 4/1994 | L'Esperance, Jr. |
| 5,338,291 A | 8/1994 | Speckman et al. |
| 5,360,339 A | 11/1994 | Rosenberg |
| 5,370,607 A | 12/1994 | Memmen |
| 5,476,445 A | 12/1995 | Baerveldt et al. |
| 5,516,522 A | 5/1996 | Peyman et al. |
| 5,520,631 A | 5/1996 | Nordquist et al. |
| 5,558,629 A | 9/1996 | Baerveldt et al. |
| 5,558,630 A | 9/1996 | Fisher |
| 5,601,094 A | 2/1997 | Reiss |
| 5,665,093 A | 9/1997 | Atkins et al. |
| 5,665,114 A | 9/1997 | Weadock et al. |
| 5,670,161 A | 9/1997 | Healy et al. |
| 5,695,474 A | 12/1997 | Daugherty |
| 5,702,414 A | 12/1997 | Richter et al. |
| 5,704,907 A | 1/1998 | Nordquist et al. |
| 5,722,948 A | 3/1998 | Gross |
| 5,743,868 A | 4/1998 | Brown et al. |
| 5,763,491 A | 6/1998 | Brandt et al. |
| 5,868,697 A | 2/1999 | Richter et al. |
| 5,908,449 A | 6/1999 | Bruchman et al. |
| 5,932,299 A | 8/1999 | Katoot |
| 5,968,058 A | 10/1999 | Richter et al. |
| 6,007,511 A | 12/1999 | Prywes |
| 6,007,578 A | 12/1999 | Schachar |
| 6,050,970 A | 4/2000 | Baerveldt |
| 6,102,045 A | 8/2000 | Nordquist et al. |
| 6,165,210 A | 12/2000 | Lau et al. |
| 6,203,513 B1 | 3/2001 | Yaron et al. |
| 6,228,873 B1 | 5/2001 | Brandt et al. |
| 6,261,256 B1 | 7/2001 | Ahmed |
| 6,264,665 B1 | 7/2001 | Yu et al. |
| 6,280,468 B1 | 8/2001 | Schachar |
| 6,450,937 B1 | 9/2002 | Mercereau et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,510,600 B2 | 1/2003 | Yaron et al. |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,726,664 B2 | 4/2004 | Yaron et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,939,298 B2 | 9/2005 | Brown et al. |
| 6,955,656 B2 | 10/2005 | Bergheim et al. |
| 6,981,958 B1 | 1/2006 | Gharib et al. |
| 7,008,396 B1 | 3/2006 | Straub |
| 7,037,335 B2 | 5/2006 | Freeman et al. |
| 7,041,077 B2 | 5/2006 | Shields |
| 7,118,547 B2 | 10/2006 | Dahan |
| 7,135,009 B2 | 11/2006 | Tu et al. |
| 7,163,543 B2 | 1/2007 | Smedley et al. |
| 7,220,238 B2 | 5/2007 | Lynch et al. |
| 7,331,984 B2 | 2/2008 | Tu et al. |
| 7,431,710 B2 | 10/2008 | Tu et al. |
| 7,563,241 B2 | 7/2009 | Tu et al. |
| 7,625,384 B2 | 12/2009 | Eriksson et al. |
| 7,867,186 B2 | 1/2011 | Haffner et al. |
| 7,879,001 B2 | 2/2011 | Haffner et al. |
| 8,277,437 B2 | 10/2012 | Saal et al. |
| 8,308,701 B2 | 11/2012 | Horvath et al. |
| 2002/0099434 A1 | 7/2002 | Buscemi et al. |
| 2002/0133168 A1 | 9/2002 | Smedley et al. |
| 2002/0177856 A1 | 11/2002 | Richter et al. |
| 2002/0188308 A1 | 12/2002 | Tu et al. |
| 2003/0079329 A1 | 5/2003 | Yaron et al. |
| 2003/0093084 A1 | 5/2003 | Nissan et al. |
| 2003/0229303 A1 | 12/2003 | Haffner et al. |
| 2003/0236483 A1 | 12/2003 | Ren |
| 2004/0024345 A1 | 2/2004 | Gharib et al. |
| 2004/0050392 A1 | 3/2004 | Tu et al. |
| 2004/0077987 A1 | 4/2004 | Rapacki et al. |
| 2004/0088048 A1 | 5/2004 | Richter et al. |
| 2004/0147870 A1 | 7/2004 | Burns et al. |
| 2004/0254521 A1 | 12/2004 | Simon |
| 2004/0260227 A1 | 12/2004 | Lisk et al. |
| 2005/0125003 A1 | 6/2005 | Pinchuk et al. |
| 2005/0246023 A1* | 11/2005 | Yeung ........................ 623/17.11 |
| 2005/0266047 A1 | 12/2005 | Tu et al. |
| 2005/0267398 A1 | 12/2005 | Protopsaltis et al. |
| 2005/0277864 A1 | 12/2005 | Haffner et al. |
| 2006/0106370 A1 | 5/2006 | Baerveldt et al. |
| 2006/0149194 A1 | 7/2006 | Conston et al. |
| 2006/0173446 A1 | 8/2006 | Dacquay et al. |
| 2007/0118065 A1 | 5/2007 | Pinchuk et al. |
| 2007/0118066 A1 | 5/2007 | Pinchuk et al. |
| 2007/0123812 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | De Juan et al. |
| 2008/0108933 A1 | 5/2008 | Yu et al. |
| 2008/0228127 A1 | 9/2008 | Burns et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0082863 A1 | 3/2009 | Schieber et al. |
| 2009/0132040 A1 | 5/2009 | Frion et al. |
| 2010/0010416 A1 | 1/2010 | Juan, Jr. et al. |
| 2010/0087774 A1 | 4/2010 | Haffner et al. |
| 2010/0100104 A1 | 4/2010 | Yu et al. |
| 2010/0114006 A1 | 5/2010 | Baerveldt |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0234790 A1 | 9/2010 | Tu et al. |
| 2010/0274258 A1 | 10/2010 | Silvestrini et al. |
| 2010/0274259 A1 | 10/2010 | Yaron et al. |
| 2010/0280317 A1 | 11/2010 | Silvestrini et al. |
| 2011/0046536 A1 | 2/2011 | Stegmann et al. |
| 2011/0105990 A1 | 5/2011 | Silvestrini |
| 2011/0118745 A1 | 5/2011 | Yu et al. |
| 2011/0230890 A1 | 9/2011 | Thyzel |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123436 A1 | 5/2012 | Reitsamer et al. |
| 2012/0123437 A1 | 5/2012 | Horvath et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0197175 A1 | 8/2012 | Horvath et al. |
| 2013/0149429 A1 | 6/2013 | Romoda et al. |
| 2013/0150770 A1 | 6/2013 | Horvath et al. |

OTHER PUBLICATIONS

U.S. Appl. No. 12/964,298, filed Dec. 9, 2010, inventors Yu et al.
International Search Report and Written Opinion for PCT/US2011/060817 dated Feb. 29, 2012.

* cited by examiner

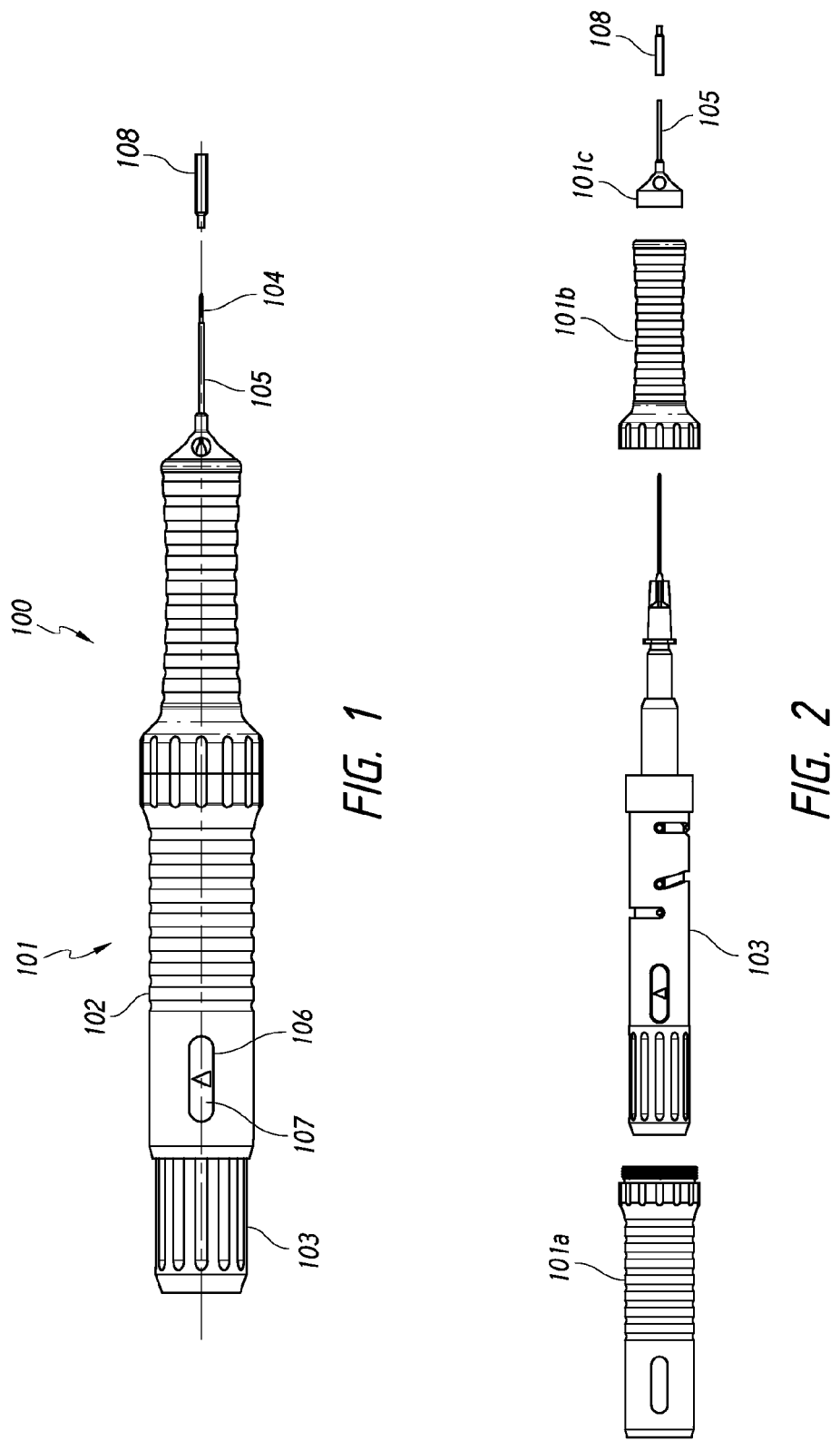

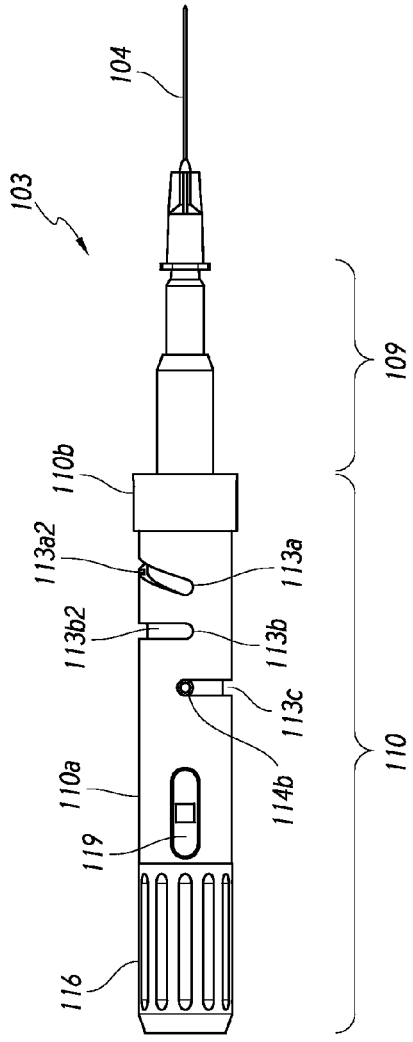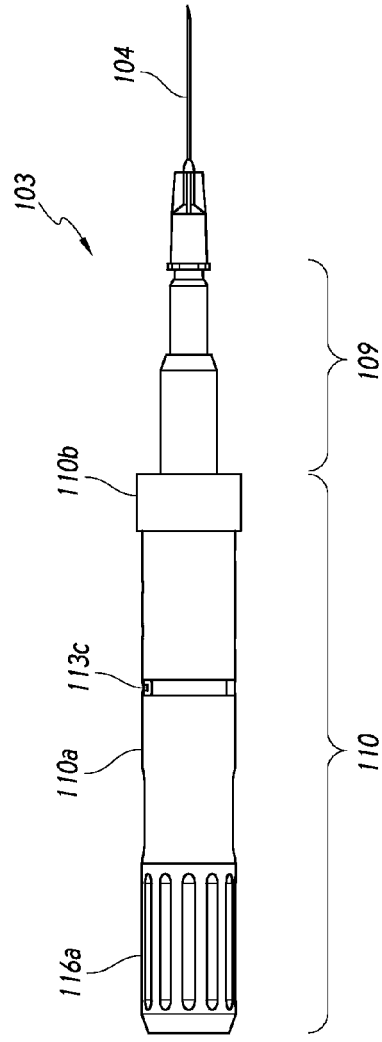
FIG. 3C
FIG. 3D

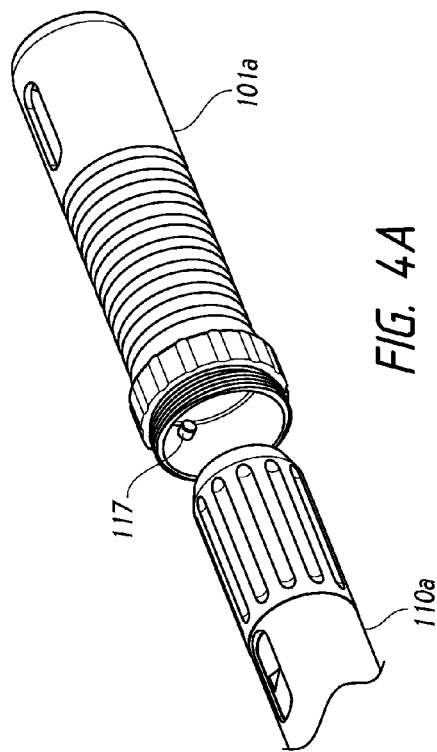
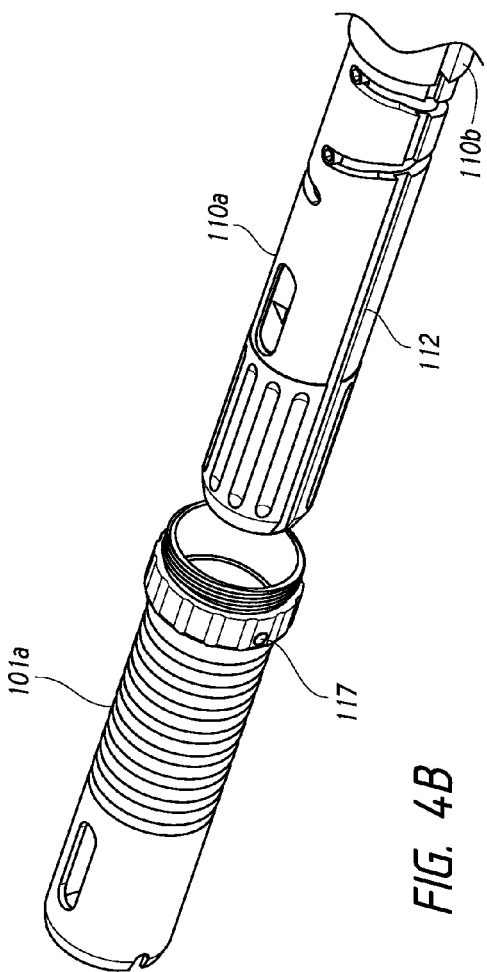
FIG. 4A
FIG. 4B

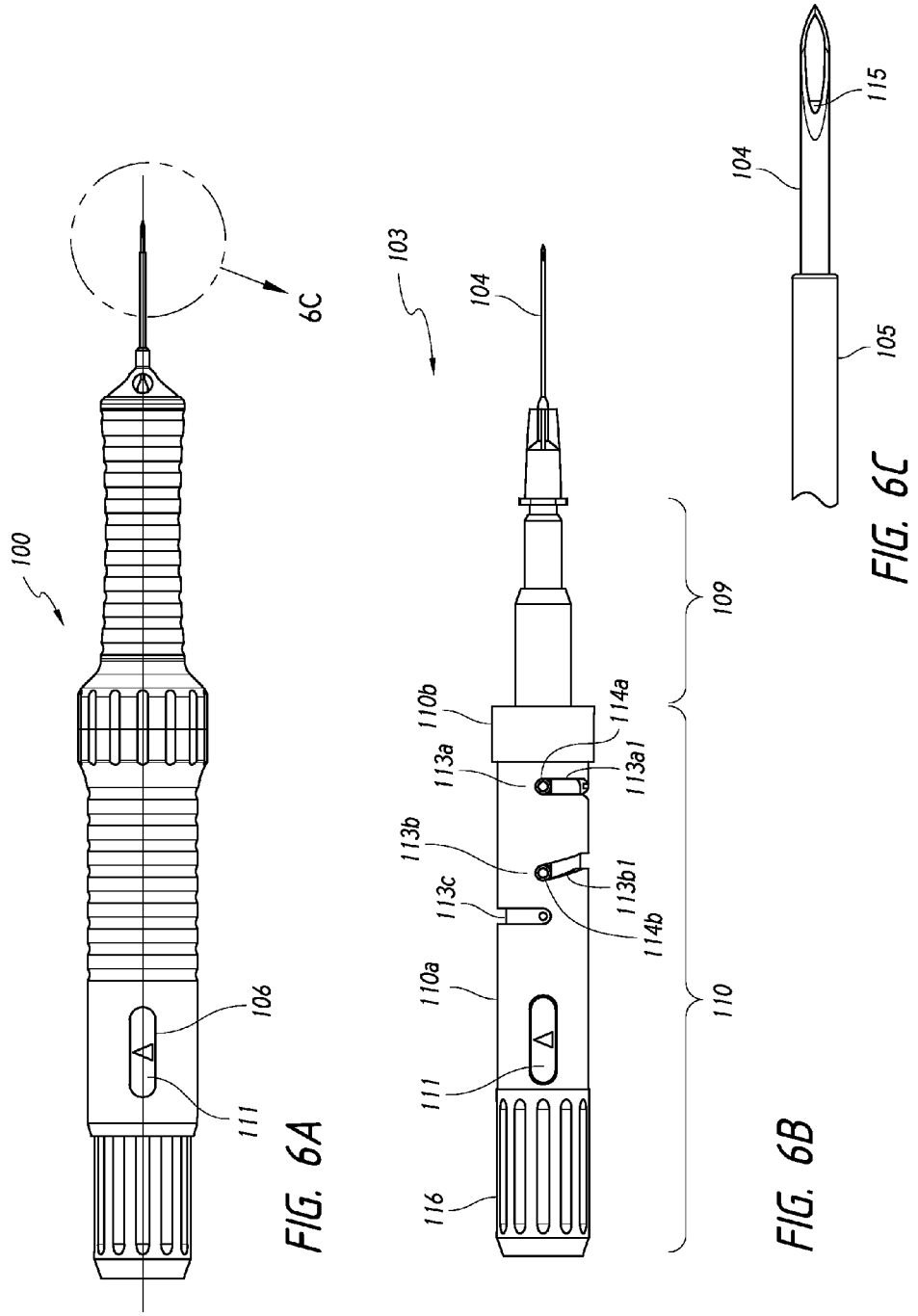

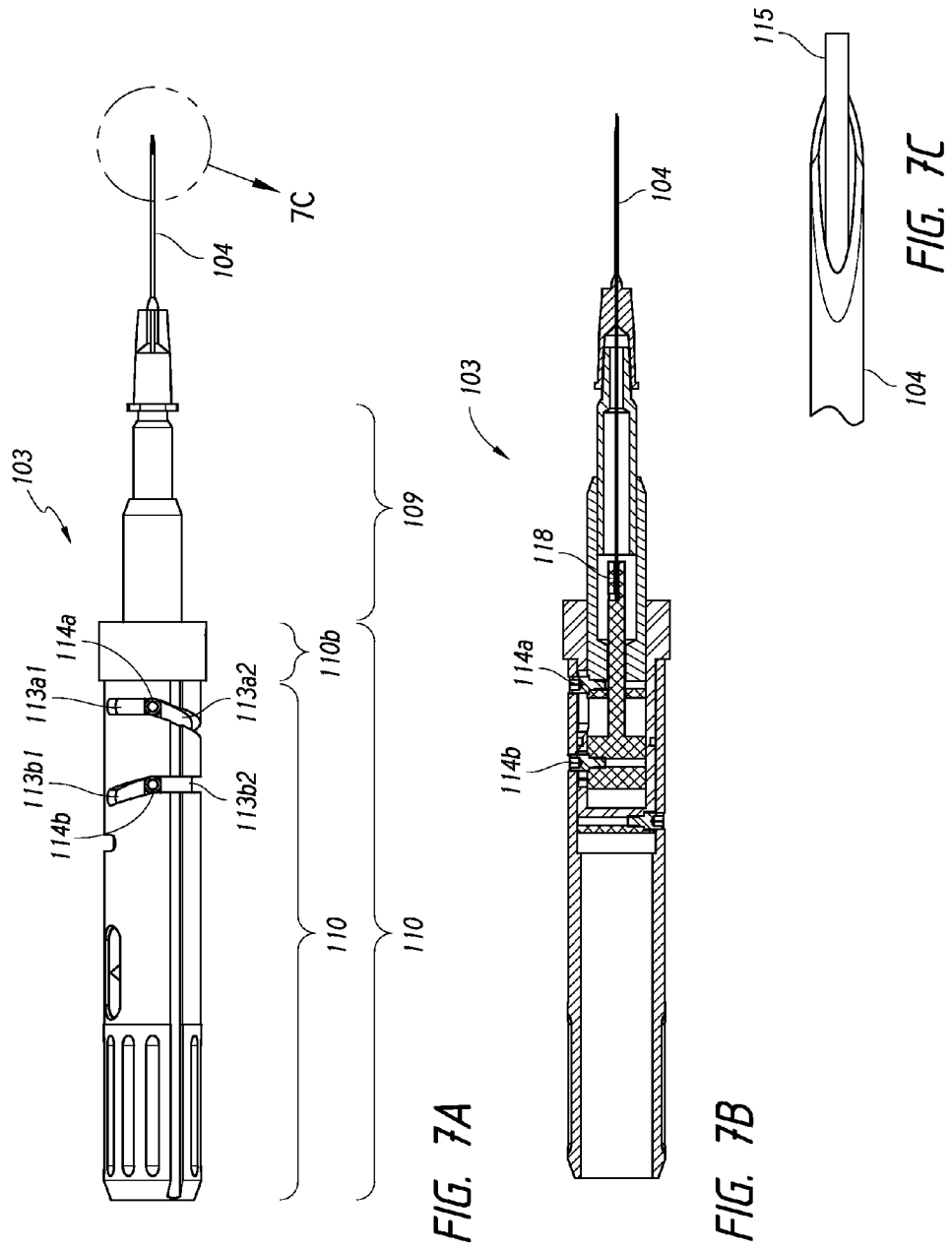

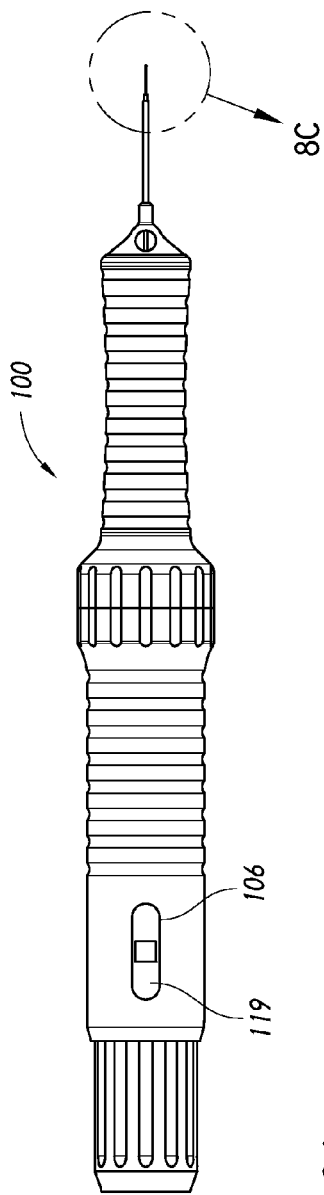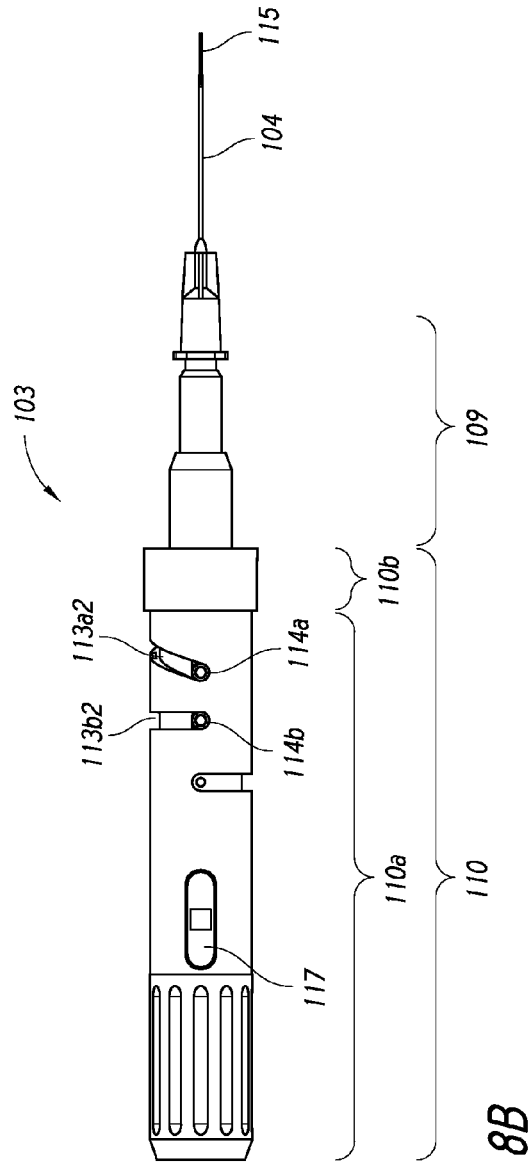

INTRAOCULAR SHUNT DEPLOYMENT DEVICES

FIELD OF THE INVENTION

The invention generally relates to devices for deploying an intraocular shunt within an eye.

BACKGROUND

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

Glaucoma may be treated by surgical intervention that involves placing a shunt in the eye to result in production of fluid flow pathways between the anterior chamber and various structures of the eye involved in aqueous humor drainage (e.g., Schlemm's canal, the sclera, or the subconjunctival space). Such fluid flow pathways allow for aqueous humor to exit the anterior chamber. Generally, the surgical intervention to implant the shunt involves inserting into the eye a deployment device that holds an intraocular shunt, and deploying the shunt within the eye. A deployment device holding the shunt enters the eye through a cornea (ab interno approach), and is advanced across the anterior chamber. The deployment device is advanced through the sclera until a distal portion of the device is in proximity to a drainage structure of the eye. The shunt is then deployed from the deployment device, producing a conduit between the anterior chamber and various structures of the eye involved in aqueous humor drainage (e.g., Schlemm's canal, the sclera, or the subconjunctival space). See for example, Prywes (U.S. Pat. No. 6,007,511).

A problem associated with such surgical interventions is ensuring that placement of the shunt does not change during deployment of the shunt from the deployment device. Deployment devices that are used to place the shunt in the eye generally rely on multiple moving components in order to deploy the shunt. Movement of the components of the deployment device shifts the position of the deployment device within the eye during the deployment process, and thus shifts the position of the shunt as it is being deployed. Such movement leads to improper placement of the shunt within the eye.

SUMMARY

The invention generally relates to deployment devices that are designed to minimize movement of the device during deployment of an intraocular shunt from the device, thereby ensuring proper placement of the shunt within the eye.

In certain aspects, deployment devices of the invention include a housing, a deployment mechanism at least partially disposed within the housing, and a hollow shaft coupled to the deployment mechanism, in which the shaft is configured to hold an intraocular shunt. With such devices, rotation of the deployment mechanism results in deployment of the shunt. Such rotational movement is translated into axial movement for deploying the shunt from the device. By utilizing rotational movement for the deployment mechanism, axial movement of the deployment device is minimized, ensuring proper placement of the shunt within the eye.

Other aspects of the invention provide devices for deploying an intraocular shunt including a housing, a deployment mechanism at least partially disposed within the housing, in which the deployment mechanism includes a two stage system, and a hollow shaft coupled to the deployment mechanism, in which the shaft is configured to hold an intraocular shunt.

Another aspect of the invention includes devices for deploying an intraocular shunt including a housing, a deployment mechanism at least partially disposed within the housing, and a hollow shaft coupled inside the housing to the deployment mechanism, wherein the shaft is configured to hold an intraocular shunt, in which the device includes an insertion configuration and a deployment configuration and the deployment configuration includes a proximal portion of the shaft being at least partially retracted to within the housing. In certain embodiments, the insertion configuration includes a distal portion of the shaft being disposed within the housing and a proximal portion of the shaft extending beyond the housing.

In certain embodiments, the shaft is configured to at least partially retract to within the housing. However, it will be appreciated that the shaft may fully retract to within the housing. In certain embodiments, the device further includes the intraocular shunt. The shunt may be completely disposed within the hollow shaft of the device. Alternatively, the shunt is partially disposed within the hollow shaft of the device.

The deployment mechanism may include a two stage system. In such embodiments, the first stage is a pusher component and the second stage is a retraction component. In this embodiment, rotation of the deployment mechanism sequentially engages the pusher component and then the retraction component. The pusher component pushes the shunt to partially deploy the shunt from within the shaft, and the retraction component retracts the shaft from around the shunt, thereby deploying the shunt. In certain embodiments, the deployment mechanism may additionally include at least one member that limits axial movement of the shaft.

The hollow shaft of the deployment device may include a beveled distal end. An exemplary hollow shaft is a needle. Devices of the invention may be completely automated, partially automated, or completely manual. Devices of the invention may be connected to larger robotic systems or may be used as stand alone handheld deployment devices. In particular embodiments, the device is a handheld device.

Devices of the invention may include an indicator that provides feedback to an operator as to the state of the deployment mechanism. The indicator may be any type of indicator know in the art, for example a visual indicator, an audio indicator, or a tactile indicator. In certain embodiments, the indicator is a visual indicator.

Aspects of the invention also include methods for deploying an intraocular shunt within an eye. These methods involve using devices described herein to deploy an intraocular shunt from the device within the eye. Generally, deploying the shunt results in a flow path from an anterior chamber of the eye to an area of lower pressure. Exemplary areas of lower pressure include intra-tenon's space, the subconjunctival space, the episcleral vein, the suprachoroidal space, and Schlemm's canal. In certain embodiments, the area of lower pressure is the subarachnoid space.

Any of a variety of methods known in the art may be used to insert devices of the invention into an eye. In certain embodiments, devices of the invention may be inserted into the eye using an ab externo approach (entering through the conjunctiva) or an ab interno approach (entering through the cornea).

BRIEF DESCRIPTION OF THE DRAWINGS

FIG. 1 is a schematic showing an embodiment of a shunt deployment device according to the invention FIG. 2 shows an exploded view of the device shown in FIG. 1.

FIGS. 3A to 3D are schematics showing different enlarged views of the deployment mechanism of the deployment device.

FIGS. 4A to 4C are schematics showing interaction of the deployment mechanism with a portion of the housing of the deployment device.

FIGS. 6A and 6B show schematics of the deployment mechanism in a pre-deployment configuration. FIG. 6C shows an enlarged view of the distal portion of the deployment device of FIG. 6A. This figure shows an intraocular shunt loaded within a hollow shaft of the deployment device.

FIGS. 7A and 7B show schematics of the deployment mechanism at the end of the first stage of deployment of the shunt from the deployment device. FIG. 7C shows an enlarged view of the distal portion of the deployment device of FIG. 7A. This figure shows an intraocular shunt partially deployed from within a hollow shaft of the deployment device.

FIG. 8A shows a schematic of the deployment device after deployment of the shunt from the device. FIG. 8B show a schematic of the deployment mechanism at the end of the second stage of deployment of the shunt from the deployment device.

DETAILED DESCRIPTION

Figure 3A:
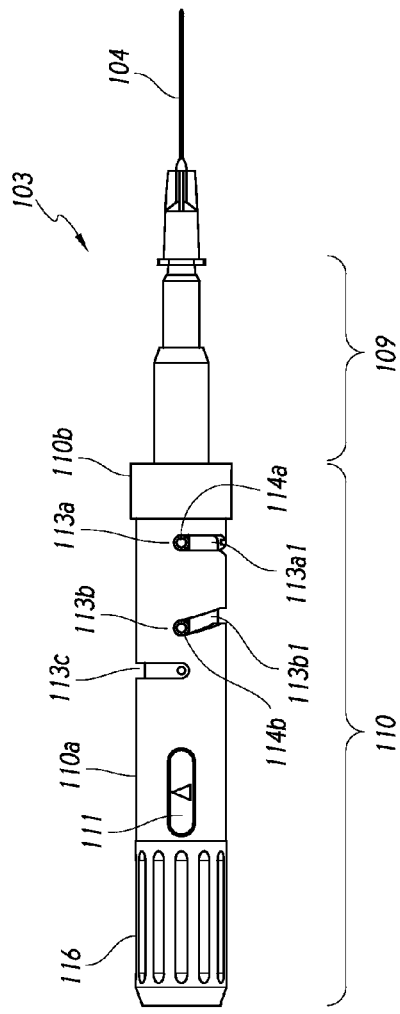
Figure 3B:
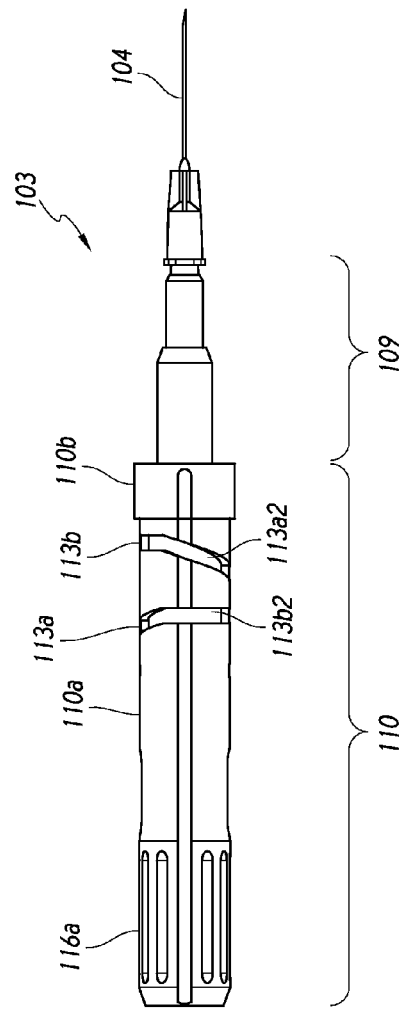

Reference is now made to FIG. 1, which shows an embodiment of a shunt deployment device 100 according to the invention. While FIG. 1 shows a handheld manually operated shunt deployment device, it will be appreciated that devices of the invention may be coupled with robotic systems and may be completely or partially automated. As shown in FIG. 1, deployment device 100 includes a generally cylindrical body or housing 101, however, the body shape of housing 101 could be other than cylindrical. Housing 101 may have an ergonomical shape, allowing for comfortable grasping by an operator. Housing 101 is shown with optional grooves 102 to allow for easier gripping by a surgeon.

Housing 101 is shown having a larger proximal portion that tapers to a distal portion. The distal portion includes a hollow sleeve 105. The hollow sleeve 105 is configured for insertion into an eye and to extend into an anterior chamber of an eye. The hollow sleeve is visible within an anterior chamber of an eye. The sleeve 105 provides a visual preview for an operator as to placement of the proximal portion of the shunt within the anterior chamber of an eye. Additionally, the sleeve 105 provides a visual reference point that may be used by an operator to hold device 100 steady during the shunt deployment process, thereby assuring optimal longitudinal placement of the shunt within the eye.

The sleeve may include an edge at a distal end that provides resistance feedback to an operator upon insertion of the deployment device 100 within an eye of a person. Upon advancement of the device 100 across an anterior chamber of the eye, the hollow sleeve 105 will eventually contact the sclera, providing resistance feedback to an operator that no further advancement of the device 100 is necessary. The edge of the sleeve 105, prevents the shaft 104 from accidentally being pushed too far through the sclera. A temporary guard 108 is configured to fit around sleeve 105 and extend beyond an end of sleeve 105. The guard is used during shipping of the device and protects an operator from a distal end of a hollow shaft 104 that extends beyond the end of the sleeve 105. The guard is removed prior to use of the device.

Housing 101 is open at its proximal end, such that a portion of a deployment mechanism 103 may extend from the proximal end of the housing 101. A distal end of housing 101 is also open such that at least a portion of a hollow shaft 104 may extend through and beyond the distal end of the housing 101. Housing 101 further includes a slot 106 through which an operator, such as a surgeon, using the device 100 may view an indicator 107 on the deployment mechanism 103.

Housing 101 may be made of any material that is suitable for use in medical devices. For example, housing 101 may be made of a lightweight aluminum or a biocompatible plastic material. Examples of such suitable plastic materials include polycarbonate and other polymeric resins such as DELRIN and ULTEM. In certain embodiments, housing 101 is made of a material that may be autoclaved, and thus allow for housing 101 to be re-usable. Alternatively, device 100, may be sold as a one-time-use device (i.e., the device is disposable), and thus the material of the housing does not need to be a material that is autoclavable.

Housing 101 may be made of multiple components that connect together to form the housing. FIG. 2 shows an exploded view of deployment device 100. In this figure, housing 101, is shown having three components 101a, 101b, and 101c. The components are designed to screw together to form housing 101. FIG. 2 also shows deployment mechanism 103. The housing 101 is designed such that deployment mechanism 103 fits within assembled housing 101. Housing 101 is designed such that components of deployment mechanism 103 are movable within housing 101.

FIGS. 3A to 3D show different enlarged views of the deployment mechanism 103. Deployment mechanism 103 may be made of any material that is suitable for use in medical devices. For example, deployment mechanism 103 may be made of a lightweight aluminum or a biocompatible plastic material. Examples of such suitable plastic materials include polycarbonate and other polymeric resins such as DELRIN and ULTEM. In certain embodiments, deployment mechanism 103 is made of a material that may be autoclaved, and thus allow for deployment mechanism 103 to be re-usable. Alternatively, device 100 may be sold as a one-time-use device (i.e., the device is disposable), and thus the material of the deployment mechanism does not need to be a material that is autoclavable.

Deployment mechanism 103 includes a proximal portion 109 and a distal portion 110. The deployment mechanism 103 is configured such that proximal portion 109 is movable within distal portion 110. More particularly, proximal portion 109 is capable of partially retracting to within distal portion 110.

In this embodiment, the proximal portion 109 is shown to taper to a connection with a hollow shaft 104. This embodiment is illustrated such that the connection between the hollow shaft 104 and the proximal portion 109 of the deployment mechanism 103 occurs inside the housing 101. In other embodiments, the connection between hollow shaft 104 and the proximal portion 109 of the deployment mechanism 103 may occur outside of the housing 101. Hollow shaft 104 may be removable from the proximal portion 109 of the deployment mechanism 103. Alternatively, the hollow shaft 104 may be permanently coupled to the proximal portion 109 of the deployment mechanism 103.

Figure 10:
FIG. 10 depicts a schematic of an exemplary intraocular shunt.

Generally, hollow shaft 104 is configured to hold an intraocular shunt 115. An exemplary intraocular shunt 115 in shown in FIG. 10. Other exemplary intraocular shunts are shown in Yu et al. (U.S. patent application number 2008/0108933). Generally, in one embodiment, intraocular shunts are of a cylindrical shape and have an outside cylindrical wall and a hollow interior. The shunt may have an inner diameter of approximately 50 µm to approximately 250 µm, an outside diameter of approximately 190 µm to approximately 300 µm, and a length of approximately 0.5 mm to about 20 mm. Thus, hollow shaft 104 is configured to at least hold a shunt of such shape and such dimensions. However, hollow shaft 104 may be configured to hold shunts of different shapes and different dimensions than those described above, and the invention encompasses a shaft 104 that may be configured to hold any shaped or dimensioned intraocular shunt. In particular embodiments, the shaft has an inner diameter of approximately 200 µm to approximately 400 µm.

The shaft 104 may be any length. A usable length of the shaft may be anywhere from about 5 mm to about 40 mm, and is 15 mm in certain embodiments. In certain embodiments, the shaft is straight. In other embodiments, shaft is of a shape other than straight, for example a shaft having a bend along its length or a shaft having an arcuate portion. Exemplary shaped shafts are shown for example in Yu et al. (U.S. patent application number 2008/0108933).

In particular embodiments, the shaft includes a bend at a distal portion of the shaft. In other embodiments, a distal end of the shaft 104 is beveled or is sharpened to a point to assist in piercing the sclera and advancing the distal end of the shaft 104 through the sclera. In particular embodiments, the distal end of the shaft 104 has a double bevel. The double bevel provides an angle at the distal end of the shaft 104 such that upon entry of the shaft into intra-Tenon's space, the distal end of shaft 104 will by parallel with Tenon's capsule and will thus not pierce Tenon's capsule and enter the subconjunctival space. This ensures proper deployment of the shunt such that a distal end of the shunt 115 is deployed within the intra-Tenon's space, rather than deployment of the distal end of the shunt 115 within the subconjunctival space. Changing the angle of the bevel allows for placement of shunt 115 within other areas of lower pressure than the anterior chamber, such as the subconjunctival space. It will be understood that implanting into intra-Tenon's space merely one embodiment of where shunt 115 may be placed within the eye, and that devices of the invention are not limited to placing shunts within intra-Tenon's space and may be used to place shunts into many other areas of the eye, such as Schlemm's canal, the subconjunctival space, the episcleral vein, or the suprachoroidal space.

The shaft 104 may hold the shunt at least partially within the hollow interior of the shaft 104. In other embodiments, the shunt is held completely within the hollow interior of the shaft 104. Alternatively, the hollow shaft may hold the shunt on an outer surface of the shaft 104. In particular embodiments, the shunt is held within the hollow interior of the shaft 104. In certain embodiments, the hollow shaft is a needle having a hollow interior. Needles that are configured to hold an intraocular shunt are commercially available from Terumo Medical Corp. (Elkington, Md.).

A distal portion of the deployment mechanism includes optional grooves 116 to allow for easier gripping by an operator for easier rotation of the deployment mechanism, which will be discussed in more detail below. The distal portion 110 of the deployment mechanism also includes at least one indicator that provides feedback to an operator as to the state of the deployment mechanism. The indicator may be any type of indicator know in the art, for example a visual indicator, an audio indicator, or a tactile indicator. FIG. 3 shows a deployment mechanism having two indicators, a ready indicator 111 and a deployed indicator 119. Ready indicator 111 provides feedback to an operator that the deployment mechanism is in a configuration for deployment of an intraocular shunt from the deployment device 100. The indicator 111 is shown in this embodiment as a green oval having a triangle within the oval. Deployed indicator 119 provides feedback to the operator that the deployment mechanism has been fully engaged and has deployed the shunt from the deployment device 100. The deployed indicator 119 is shown in this embodiment as a yellow oval having a black square within the oval. The indicators are located on the deployment mechanism such that when assembled, the indicators 111 and 119 may be seen through slot 106 in housing 101.

Figure 4C:
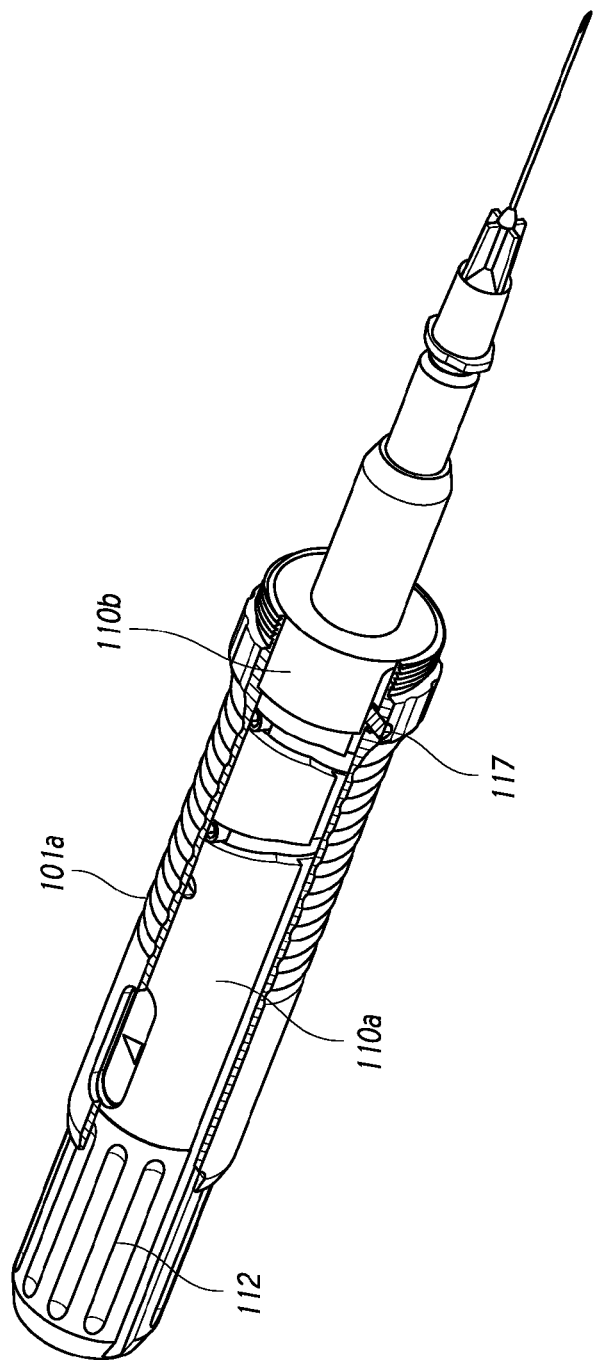

The distal portion 110 includes a stationary portion 110*b* and a rotating portion 110*a*. The distal portion 110 includes a channel 112 that runs part of the length of stationary portion 110*b* and the entire length of rotating portion 110*a*. The channel 112 is configured to interact with a protrusion 117 on an interior portion of housing component 101*a* (FIGS. 4A and 4B). During assembly, the protrusion 117 on housing component 101*a* is aligned with channel 112 on the stationary portion 110*b* and rotating portion 110*a* of the deployment mechanism 103. The distal portion 110 of deployment mechanism 103 is slid within housing component 101*a* until the protrusion 117 sits within stationary portion 110*b* (FIG. 4C). Assembled, the protrusion 117 interacts with the stationary portion 110*b* of the deployment mechanism 103 and prevents rotation of stationary portion 110*b*. In this configuration, rotating portion 110*a* is free to rotate within housing component 101*a*.

Referring back to FIG. 3, the rotating portion 110*a* of distal portion 110 of deployment mechanism 103 also includes channels 113*a*, 113*b*, and 113*c*. Channel 113*a* includes a first portion 113*a*1 that is straight and runs perpendicular to the length of the rotating portion 110*a*, and a second portion 113*a*2 that runs diagonally along the length of rotating portion 110*a*, downwardly toward a distal end of the deployment mechanism 103. Channel 113*b* includes a first portion 113*b*1 that runs diagonally along the length of the rotating portion 110*a*, upwardly toward a proximal end of the deployment mechanism 103, and a second portion that is straight and runs perpendicular to the length of the rotating portion 110*a*. The point at which first portion 113*a*1 transitions to second portion 113*a*2 along channel 113*a*, is the same as the point at which first portion 113*b*1 transitions to second portion 113*b*2 along channel 113*b*. Channel 113*c* is straight and runs perpendicular to the length of the rotating portion 110*a*. Within each of channels 113*a*, 113*b*, and 113*c*, sit members 114*a*, 114*b*, and 114*c* respectively. Members 114*a*, 114*b*, and 114*c* are movable within channels 113*a*, 113*b*, and 113*c*. Members 114a, 114b, and 114c also act as stoppers that limit movement of rotating portion 110a, which thereby limits axial movement of the shaft 104.

Figure 5:
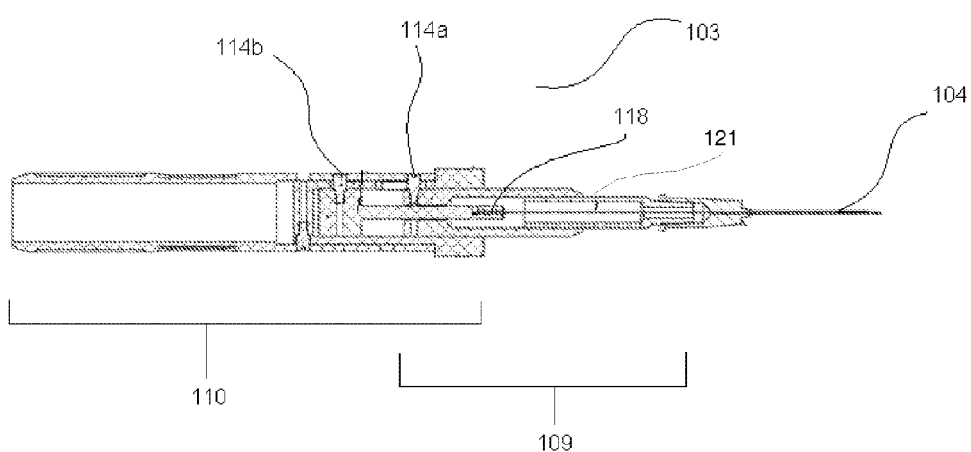
FIG. 5 shows a cross sectional view of the deployment mechanism of the deployment device.

FIG. 5 shows a cross-sectional view of deployment mechanism 103. Member 114a is connected to the proximal portion 109 of the deployment mechanism 103. Movement of member 114a results in retraction of the proximal portion 109 of the deployment mechanism 103 to within the distal portion 110 of the deployment mechanism 103. Member 114b is connected to a pusher component 118. The pusher component 118 extends through the proximal portion 109 of the deployment mechanism 103 and extends into a portion of hollow shaft 104. The pusher component is involved in deployment of a shunt from the hollow shaft 104. An exemplary pusher component is a plunger. Movement of member 114b engages pusher 118 and results in pusher 118 advancing within hollow shaft 104.

Reference is now made to FIGS. 6-8, which accompany the following discussion regarding deployment of a shunt 115 from deployment device 100. FIG. 6A shows deployment device 100 is a pre-deployment configuration. In this configuration, shunt 115 is loaded within hollow shaft 104 (FIG. 6C). As shown in FIG. 6C, shunt 115 is only partially within shaft 104, such that a portion of the shunt is exposed. However, the shunt 115 does not extend beyond the end of the shaft 104. In other embodiments, the shunt 115 is completely disposed within hollow shaft 104. The shunt 115 is loaded into hollow shaft 104 such that the shunt abuts pusher component 118 within hollow shaft 104. A distal end of shaft 104 is beveled to assist in piercing tissue of the eye.

Additionally, in the pre-deployment configuration, a portion of the shaft 104 extends beyond the sleeve 105 (FIG. 6C). The deployment mechanism is configured such that member 114a abuts a proximal end of the first portion 113a1 of channel 113a, and member 114b abut a proximal end of the first portion 113b1 of channel 113b (FIG. 6B). In this configuration, the ready indicator 111 is visible through slot 106 of the housing 101, providing feedback to an operator that the deployment mechanism is in a configuration for deployment of an intraocular shunt from the deployment device 100 (FIG. 6A). In this configuration, the device 100 is ready for insertion into an eye (insertion configuration or pre-deployment configuration). Methods for inserting and implanting shunts are discussed in further detail below.

Once the device has been inserted into the eye and advanced to a location to where the shunt will be deployed, the shunt 115 may be deployed from the device 100. The deployment mechanism 103 is a two-stage system. The first stage is engagement of the pusher component 118 and the second stage is retraction of the proximal portion 109 to within the distal portion 110 of the deployment mechanism 103. Rotation of the rotating portion 110a of the distal portion 110 of the deployment mechanism 103 sequentially engages the pusher component and then the retraction component 121.

In the first stage of shunt deployment, the pusher component is engaged and the pusher partially deploys the shunt from the deployment device. During the first stage, rotating portion 110a of the distal portion 110 of the deployment mechanism 103 is rotated, resulting in movement of members 114a and 114b along first portions 113a1 and 113b1 in channels 113a and 113b. Since the first portion 113a1 of channel 113a is straight and runs perpendicular to the length of the rotating portion 110a, rotation of rotating portion 110a does not cause axial movement of member 114a. Without axial movement of member 114a, there is no retraction of the proximal portion 109 to within the distal portion 110 of the deployment mechanism 103. Since the first portion 113b1 of channel 113b runs diagonally along the length of the rotating portion 110a, upwardly toward a proximal end of the deployment mechanism 103, rotation of rotating portion 110a causes axial movement of member 114b toward a proximal end of the device. Axial movement of member 114b toward a proximal end of the device results in forward advancement of the pusher component 118 within the hollow shaft 104. Such movement of pusher component 118 results in partially deployment of the shunt 115 from the shaft 104.

FIGS. 7A to 7C show schematics of the deployment mechanism at the end of the first stage of deployment of the shunt from the deployment device. As is shown FIG. 7A, members 114a and 114b have finished traversing along first portions 113a1 and 113b1 of channels 113a and 113b. Additionally, pusher component 118 has advanced within hollow shaft 104 (FIG. 7B), and shunt 115 has been partially deployed from the hollow shaft 104 (FIG. 7C). As is shown in these figures, a portion of the shunt 115 extends beyond an end of the shaft 104.

Figure 8C:
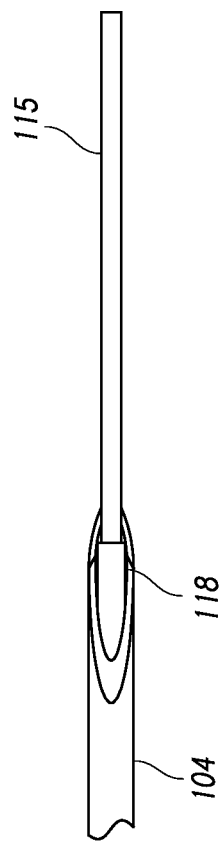
FIG. 8C shows an enlarged view of the distal portion of the deployment device after retraction of the shaft with the pusher abutting the shunt.

In the second stage of shunt deployment, the retraction component 121 is engaged and the proximal portion of the deployment mechanism is retracted to within the distal portion of the deployment mechanism, thereby completing deployment of the shunt from the deployment device. During the second stage, rotating portion 110a of the distal portion 110 of the deployment mechanism 103 is further rotated, resulting in movement of members 114a and 114b along second portions 113a2 and 113b2 in channels 113a and 113b. Since the second portion 113b2 of channel 113b is straight and runs perpendicular to the length of the rotating portion 110a, rotation of rotating portion 110a does not cause axial movement of member 114b. Without axial movement of member 114b, there is no further advancement of pusher 118. Since the second portion 113a2 of channel 113a runs diagonally along the length of the rotating portion 110a, downwardly toward a distal end of the deployment mechanism 103, rotation of rotating portion 110a causes axial movement of member 114a toward a distal end of the device. Axial movement of member 114a toward a distal end of the device results in retraction of the proximal portion 109 to within the distal portion 110 of the deployment mechanism 103. Retraction of the proximal portion 109, results in retraction of the hollow shaft 104. Since the shunt 115 abuts the pusher component 118, the shunt remains stationary at the hollow shaft 104 retracts from around the shunt 115 (FIG. 8C). The shaft 104, retracts almost completely to within the sleeve 105. During both stages of the deployment process, the sleeve 105 remains stationary and in a fixed position. During both stages of the deployment process, the housing 101 remains stationary and in a fixed position.

Figure 8D:
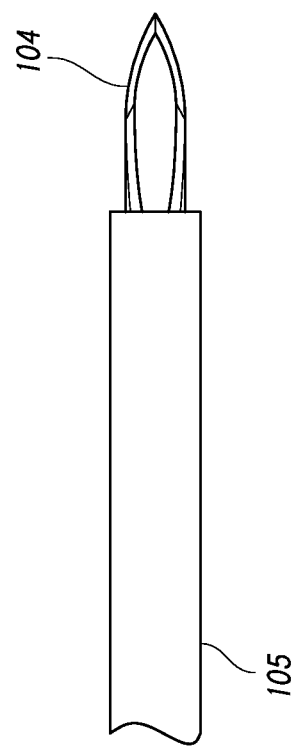
FIG. 8D shows an enlarged view of the distal portion of the deployment device after deployment of the shunt.

FIG. 8A shows a schematic of the device 100 after deployment of the shunt 115 from the device 100. FIG. 8B shows a schematic of the deployment mechanism at the end of the second stage of deployment of the shunt from the deployment device. As is shown in FIG. 8B, members 114a and 114b have finished traversing along second portions 113a1 and 113b1 of channels 113a and 113b. Additionally, proximal portion 109 has retracted to within distal portion 110, thus resulting in retraction of the hollow shaft 104 to within the sleeve 105. FIG. 8D shows an enlarged view of the distal portion of the deployment device after deployment of the shunt. This figure shows that the hollow shaft 104 is not fully retracted to within the sleeve 105 of the deployment device 100. However, in certain embodiments, the shaft 104 may completely retract to within the sleeve 105.

Referring to FIG. 8A, in the post-deployment configuration, the deployed indicator 119 is visible through slot 106 of the housing 101, providing feedback to the operator that the deployment mechanism has been fully engaged and that the shunt 115 has been deployed from the deployment device 100.

Any of a variety of methods known in the art may be used to insert devices of the invention into an eye. In certain embodiments, devices of the invention may be inserted into the eye using an ab externo approach (entering through the conjunctiva) or an ab interno approach (entering through the cornea).

In certain embodiments, devices of the invention are inserted into the eye using an ab interno approach. Ab interno approaches for implanting an intraocular shunt are shown for example in Yu et al. (U.S. Pat. No. 6,544,249 and U.S. patent application number 2008/0108933) and Prywes (U.S. Pat. No. 6,007,511), the content of each of which is incorporated by reference herein in its entirety.

Devices of the invention may be inserted into the eye to deploy shunts that create fluid drainage passageways from the anterior chamber of the eye to various drainage structures of the eye. Exemplary drainage structures include Schlemm's canal, the subconjunctival space, the episcleral vein, the suprachoroidal space, or the intra-Tenon's space. In certain embodiments, fluid is drained to the subarachnoid space.

In particular embodiments, devices of the invention are inserted into the eye to deploy shunts that create fluid drainage passageways from the anterior chamber to the intra-Tenon's space. Within an eye, there is a membrane known as the conjunctiva, and the region below the conjunctiva is known as the subconjunctival space. Within the subconjunctival space is a membrane known as Tenon's capsule. Below Tenon's capsule there are Tenon's adhesions that connect the Tenon's capsule to the sclera. The space between Tenon's capsule and the sclera where the Tenon's adhesions connect the Tenon's capsule to the sclera is known as the intra-Tenon's space.

Figure 9A:
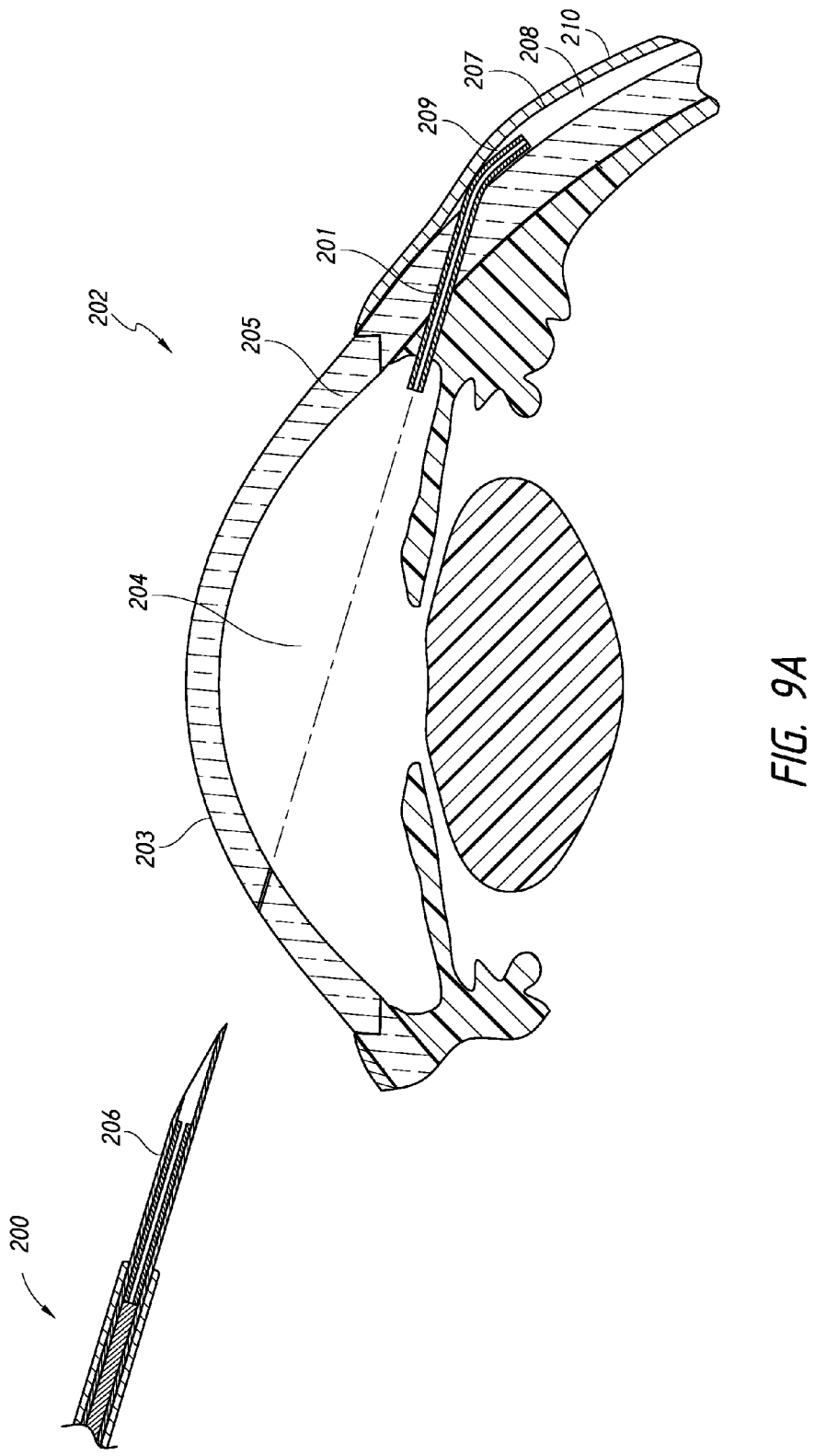
FIGS. 9A and 9B show an intraocular shunt deployed within the eye. A proximal portion of the shunt resides in the anterior chamber and a distal portion of the shunt resides within the intra-Tenon's space. A middle portion of the shunt resides in the sclera.
Figure 9B:
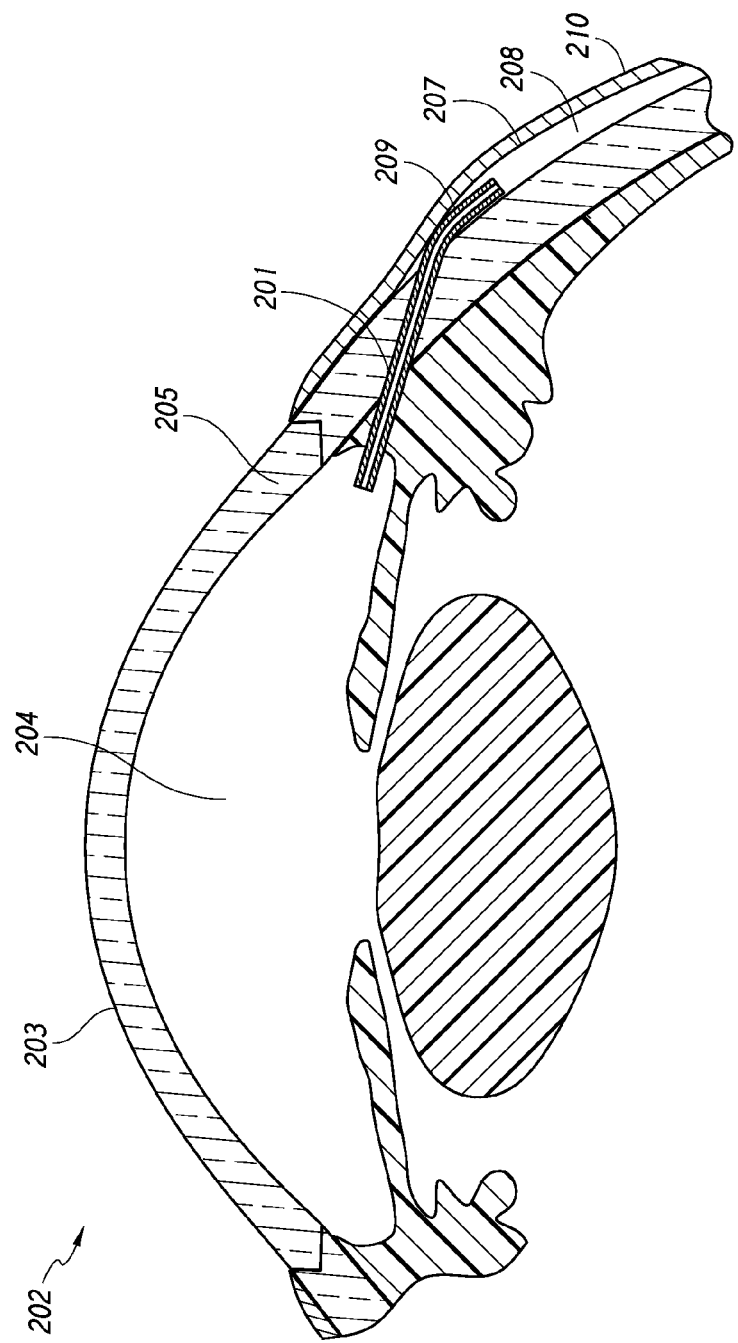

FIGS. 9A and 9B show an intraocular shunt placed into the eye using devices of the invention such that the shunt forms a passage for fluid drainage from the anterior chamber to the intra-Tenon's space. To place the shunt within the eye, a surgical intervention to implant the shunt is performed that involves inserting into the eye 202 a deployment device 200 that holds an intraocular shunt 201, and deploying at least a portion of the shunt 201 within intra-Tenon's space 208, within the subconjunctival space 209 and below the conjunctiva 210. In certain embodiments, a hollow shaft 206 of a deployment device 200 holding the shunt 201 enters the eye 202 through the cornea 203 (ab interno approach). The shaft 206 is advanced across the anterior chamber 204 (as depicted by the broken line) in what is referred to as a transpupil implant insertion. The shaft 206 is advanced through the sclera 205 until a distal portion of the shaft 206 is in proximity to Tenon's capsule 207.

Once a distal portion of the hollow shaft 206 is within the intra-Tenon's space 208, the shunt 201 is then deployed from the shaft 206 of the deployment device 200, producing a conduit between the anterior chamber 204 and the intra-Tenon's space 208 to allow aqueous humor to drain from the anterior chamber 204 (See FIGS. 9A and 9B).

Combinations of Embodiments

As will be appreciated by one skilled in the art, individual features of the invention may be used separately or in any combination. Particularly, it is contemplated that one or more features of the individually described above embodiments may be combined into a single shunt.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein.

What is claimed is:

1. A device for deploying an intraocular shunt, the device comprising:
    a housing;
    a deployment mechanism at least partially disposed within the housing, the deployment mechanism comprising (i) a rotating component having a diagonal first slot and a diagonal second slot, (ii) a pusher component having a first member that sits within the first slot, and (iii) a retraction component having a second member that sits within the second slot; and
    a hollow shaft coupled to the deployment mechanism, wherein the shaft is configured to hold an intraocular shunt;
    wherein rotation of the rotating component causes distal axial movement of the first member thereby urging the pusher component in a distal axial direction to advance the shunt partially from within the shaft, and
    wherein further rotation of the rotating component causes proximal axial movement of the second member thereby urging the retraction component in a proximal axial direction to retract the shaft from around the shunt, thereby exposing the shunt.

2. The device according to claim 1, wherein the shaft is configured to at least partially retract to within the housing.

3. The device according to claim 2, wherein the shaft fully retracts to within the housing.

4. The device according to claim 1, further comprising an intraocular shunt that is at least partially disposed within the shaft.

5. The device according to claim 1, wherein the deployment mechanism further comprises at least one member that limits axial movement of the shaft.

6. The device according to claim 1, wherein a distal end of the shaft is beveled.

7. The device according to claim 1, wherein the hollow shaft is a needle.

8. The device according to claim 1, wherein the device is a handheld device.

9. The device according to claim 1, further comprising an indicator formed on the housing and the deployment mechanism that provides feedback to an operator as to the state of the deployment mechanism.

10. The device according to claim 9, wherein the indicator comprises a slot formed in the housing and extending along the deployment mechanism for providing a visual indication of the state of the deployment mechanism.

11. The device according to claim 1, wherein a distal portion of the housing comprises a sleeve and the hollow shaft is movable within the sleeve.

12. The device according to claim 11, wherein a distal end of the sleeve comprises a stopping edge.

13. The device according to claim 11, wherein the sleeve is visible within the eye.

14. The device according to claim 13, wherein the sleeve provides a visual preview for an operator as to placement of a proximal portion of the shunt within an anterior chamber of an eye.

15. The device according to claim 13, wherein the sleeve provides a visual reference point that may be used by an operator to hold the device steady during deployment of the shunt from the device.

16. The device according to claim 1, wherein the device is disposable.

17. A device for deploying an intraocular shunt, the device comprising:
   a housing;
   a deployment mechanism at least partially disposed within the housing, the deployment mechanism comprising (i) a rotating component having a diagonal first slot and a diagonal second slot, (ii) a pusher component having a first member that sits within the first slot, and (iii) a retraction component having a second member that sits within the second slot, the rotating component of the deployment mechanism being configured to sequentially engage the pusher component and then the retraction component; and
   a hollow shaft coupled to the deployment mechanism, wherein the shaft is configured to hold an intraocular shunt;
   wherein rotation of the rotating component causes distal axial movement of the first member thereby urging the pusher component in a distal axial direction to advance the shunt out of the shaft, and
   wherein further rotation of the rotating component causes proximal axial movement of the second member thereby urging the retraction component in a proximal axial direction to retract the shaft from around the shunt at least partially into the housing while the pusher component limits axial movement of the shunt, thereby exposing the shunt.

18. The device according to claim 17, wherein the shaft fully retracts to within the housing.

19. The device according to claim 17, further comprising an intraocular shunt that is at least partially disposed within the shaft.

20. The device according to claim 17, wherein the deployment mechanism further comprises at least one member that limits axial movement of the shaft.

21. The device according to claim 17, wherein a distal end of the shaft is beveled.

22. The device according to claim 17, wherein the hollow shaft is a needle.

23. The device according to claim 17, wherein the device is a handheld device.

24. The device according to claim 17, further comprising an indicator formed on the housing and the deployment mechanism that provides feedback to an operator as to the state of the deployment mechanism.

25. The device according to claim 24, wherein the indicator comprises a slot formed in the housing and extending along the deployment mechanism for providing a visual indication of the state of the deployment mechanism.

26. The device according to claim 17, wherein a distal portion of the housing comprises a sleeve and the hollow shaft is movable within the sleeve.

27. The device according to claim 26, wherein a distal end of the sleeve comprises a stopping edge.

28. The device according to claim 26, wherein the sleeve is visible within the eye.

29. The device according to claim 28, wherein the sleeve provides a visual preview for an operator as to placement of a proximal portion of the shunt within an anterior chamber of an eye.

30. The device according to claim 28, wherein the sleeve provides a visual reference point that may be used by an operator to hold the device steady during deployment of the shunt from the device.

31. The device according to claim 17, wherein the device is disposable.

32. A device for deploying an intraocular shunt, the device comprising:
   a housing;
   a deployment mechanism at least partially disposed within the housing, the deployment mechanism comprising (i) a rotating component having a diagonal first slot and a diagonal second slot, (ii) a pusher component having a first member that sits within the first slot, and (iii) a retraction component having a second member that sits within the second slot, the rotating component of the deployment mechanism being configured to sequentially engage the pusher component and then the retraction component; and
   a hollow shaft coupled inside the housing to the deployment mechanism, wherein the shaft is configured to hold an intraocular shunt;
   wherein the device comprises an insertion configuration in which rotation of the rotating component causes distal axial movement of the first member thereby urging the pusher component in a distal direction to advance the shunt from within the shaft and a deployment configuration in which further rotation of the rotating component causes proximal axial movement of the second member thereby urging the retraction component in a proximal axial direction to retract the shaft from around the shunt at least partially retracted into the housing relative to the pusher component, thereby exposing the shunt.

33. The device according to claim 32, the shaft fully retracts to within the housing.

34. The device according to claim 32, further comprising an intraocular shunt that is at least partially disposed within the shaft.

35. The device according to claim 32, wherein the insertion configuration comprises a distal portion of the shaft being disposed within the housing and a proximal portion of the shaft extending beyond the housing.

36. The device according to claim 32, wherein the deployment mechanism further comprises at least one member that limits axial movement of the shaft.

37. The device according to claim 32, wherein a distal end of the shaft is beveled.

38. The device according to claim 32, wherein the hollow shaft is a needle.

39. The device according to claim 32, wherein the device is a handheld device.

40. The device according to claim 32, further comprising an indicator formed on the housing and the deployment mechanism that provides feedback to an operator as to the state of the deployment mechanism.

41. The device according to claim 40, wherein the indicator comprises a slot formed in the housing and extending along the deployment mechanism for providing a visual indication of the state of the deployment mechanism.

42. The device according to claim 32, wherein a distal portion of the housing comprises a sleeve and the hollow shaft is movable within the sleeve.

43. The device according to claim 42, wherein a distal end of the sleeve comprises a stopping edge.

44. The device according to claim 32, wherein the device comprises a material that is not autoclavable.

* * * * *